United States Patent [19]

Pitt

[11] 4,071,423
[45] Jan. 31, 1978

[54] USE OF FREE RADICAL INITIATORS IN THIOLCARBAMATE PREPARATION

[75] Inventor: Harold M. Pitt, Lafayette, Calif.

[73] Assignee: Stauffer Chemical Company, Westport, Conn.

[21] Appl. No.: 792,364

[22] Filed: Apr. 29, 1977

[51] Int. Cl.² .................. B01J 1/10; C07C 155/02; C07C 155/03
[52] U.S. Cl. ............... 204/158 R; 204/162 R; 260/455 A
[58] Field of Search .............. 204/158 R, 162 R; 260/455 A

[56] References Cited

U.S. PATENT DOCUMENTS

| | | | |
|---|---|---|---|
| 3,477,933 | 11/1969 | Stamm et al. | 204/158 R |
| 3,520,903 | 7/1970 | Pierce | 204/158 R |
| 3,954,729 | 4/1976 | Sato et al. | 260/455 A |

*Primary Examiner*—Howard S. William
*Attorney, Agent, or Firm*—M. Henry Heines

[57] ABSTRACT

Thiolcarbmates are prepared by a process comprising reacting an amine of the formula

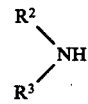

with carbonyl sulfide and an unsaturated compound selected from the group consisting of $CH_2=C=CR^4R^5$, $CH_2=CH-R^6$, and

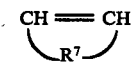

in which
$R^2$ and $R^3$ are independently selected from the group consisting of the following substituted or unsubstituted groups: alkyl, alkenyl, alkynyl, aralkyl, and cycloalkyl; or
$R^2$ and $R^3$ joined to each other form, together with the nitrogen atom, a nitrogen-containing heterocyclic ring;
$R^4$, $R^5$, and $R^6$ are independently selected from the group consisting of hydrogen and the following substituted or unsubstituted groups: alkyl, alkenyl, alkynyl, aryl, aralkyl, cycloalkyl, cycloalkenyl, alkoxy, alkenoxy, alkoxyalkyl, alkylthioalkyl, alkoxyalkenyl, alkylthioalkenyl, and heterocyclic ring groups; and
$R^7$ is alkylene or alkenylene;

in the presence of at least one free radical initiator selected from the group consisting of an azonitrile, a phosphite, a ketone, a dione, and a substituted or unsubstituted aromatic compound.

12 Claims, No Drawings

USE OF FREE RADICAL INITIATORS IN THIOLCARBAMATE PREPARATION

BACKGROUND OF THE INVENTION

The esters of Thiolcarbamic acids are useful for a variety of purposes. Some are active herbicides, others are effective for inhibiting the growth of micro-organisms such as bacteria, and still others are active insecticides. The following is a group of processes representative of those known in the art for the preparation of these compounds.

The process of U.S. Pat. No. 2,983,747 employs zinc chloride as a catalyst in the direct reaction of carbamyl chlorides with mercaptans to produce various thiocarbamic esters. Although the reaction can be conducted without the use of a solvent, a solvent inert to the catalyst, such as an organic solvent, must be used if a solvent is employed.

U.S. Pat. No. 2,913,327 teaches a process involving the preparation of the sodium salt of a mercaptan followed by reaction with a carbamyl chloride in the presence of a solvent. The use of the sodium salt of the mercaptan causes problems of filtration and solids handling. The use of a solvent reduces reactor capacity throughout and can create a recovery problem. Furthermore, the hydrogen evolved during the preparation of the sodium salt causes a disposal problem.

U.S. Pat. No. 3,836,524 describes a process involving the reaction of a carbamyl chloride with a mercaptan in the presence of an aqueous solution of a caustic agent. This process requires considerable agitation in order to form a high interfacial area between the two liquid phases, as well as a high caustic concentration in order to achieve the desired conversion and product purity.

U.S. Pat. No. 3,133,947 describes a process which comprises reacting a secondary or primary amine with carbonyl sulfide in the presence of a basic material which may be any amine, including a tertiary amine, and thereafter reacting the intermediate with an organic sulfate, such as a dialkyl sulfate, or a diallyl sulfate. Alkyl sulfate values are lost in this process, thus adding to the overall expense.

U.S. Pat. No. 3,151,119 describes a process involving reacting an amine with carbon monoxide and sulfur, followed by alkylation with an alkylating agent at temperatures below 20° C.

Carbonyl sulfide is reacted with a primary or secondary amine in aqueous alkaline solution at temperatures of 20° C or below in the process taught by U.S. Pat. No. 3,167,571. Condensation of the amine salt of the thiocarbamic acid is then effected by reaction of the salt with an organic halide.

In the process described in U.S. Pat. No. 3,954,729, a secondary amine is reacted with carbonyl sulfide in the presence of an aromatic solvent to form an amine salt of a thiocarbamic acid, which is then reacted with an alkyl halide to form the thiocarbamic acid ester.

It has been discovered that a novel process can be used for the preparation of thiolcarbamates. The object of this invention is to provide such a process, as will be more fully explained hereinbelow.

SUMMARY AND SCOPE OF THE INVENTION

The present invention provides a novel process for the preparation of substituted thiolcarbamic acid esters, also known in the art as thiolcarbamates. In particular, this invention relates to the use of certain free radical initiators in the preparation of thiolcarbamates.

Thiolcarbamates which are prepared by the process of the present invention are those corresponding to the following general formula:

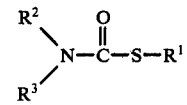

in which
$R^1$ is selected from the group consisting of $-CH_2-CH=CR^4R^5$, $-CH_2-CH_2-R^6$, and

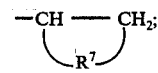

$R^2$ and $R^3$ are independently selected from the group consisting of the following substituted or unsubstituted groups: $C_1$-$C_{10}$ alkyl, $C_2$-$C_6$ alkenyl, $C_2$-$C_4$ alkynyl, aralkyl containing a $C_1$-$C_6$ alkyl, and $C_3$-$C_7$ cycloalkyl; wherein the substituents are independently selected from the group consisting of halo, cyano, nitro, trifluoromethyl, $C_1$-$C_4$ alkoxy, and $C_1$-$C_4$ alkyl; or $R^2$ and $R^3$ are joined to each other to form, together with the nitrogen atom, a nitrogen-containing heterocyclic ring;

$R^4$, $R^5$, and $R^6$ are independently selected from the group consisting of hydrogen and the following substituted or unsubstituted groups; $C_1$-$C_{10}$ alkyl, $C_2$-$C_6$ alkenyl, $C_2$-$C_4$ alkynyl, aryl, aralkyl containing a $C_1$-$C_6$ alkyl, $C_3$-$C_7$ cycloalkyl, $C_5$-$C_7$ cycloalkenyl, $C_1$-$C_{10}$ alkoxy, $C_2$-$C_6$ alkenoxy, $C_2$-$C_{10}$ alkoxyalkyl, $C_2$-$C_{10}$ alkylthioalkyl, $C_3$-$C_{10}$ alkoxyalkenyl, $C_3$-$C_{10}$ alkylthioalkenyl, and heterocyclic ring groups; wherein the substituents are independently selected from the group consisting of halo, cyano, nitro, trifluoromethyl, $C_1$-$C_4$ alkoxy, and $C_1$-$C_4$ alkyl; and $R^7$ is selected from the group consisting of $C_1$-$C_5$ alkylene and $C_3$-$C_5$ alkenylene.

The above are intended to include both mono- and multi-substituted groups with the same or different substituents, where substituents are indicated.

According to the process of the invention, a secondary amine of the formula

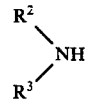

is reacted with carbonyl sulfide and an unsaturated compound selected from the group consisting of $CH_2=C=CR^4R^5$, $CH_2=C-R^6$, and

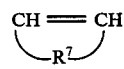

in the presence of a free radical initiator. The symbols $R^2$, $R^3$, $R^4$, $R^5$, $R^6$, and $R^7$ are as defined above.

Within the scope of the above-defined general formulae, the following substituent combinations are preferred:

$R^1$ is selected from the group consisting of

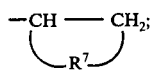

$R^2$ and $R^3$ are independently selected from the group consisting of $C_1$-$C_5$ alkyl, $C_2$-$C_4$ alkenyl, and $C_4$-$C_6$ cycloalkyl, or $R^2$ and $R^3$ joined together with the nitrogen atom to which they are attached form the group

in which $R^\circ$ is $C_4$-$C_6$ alkylene;

$R^6$ is selected from the group consisting of hydrogen and $C_1$-$C_3$ alkyl; and $R^7$ is $C_3$-$C_5$ alkylene.

Examples of such amines which are useful in the present invention are dimethylamine, diethylamine, di-n-propylamine, diisobutylamine, di-t-butylamine, methylethylamine, methylbutylamine, ethylbutylamine, diallylamine, bis-(2-methoxyethyl)amine, bis-(2-phenoxyethyl)amine, N-ethylcyclohexylamine, pyrrolydine, piperidine, azepine, hexahydro-1H-azepine, and ethylphenylamine.

Examples of unsaturated compounds useful in the present invention are ethylene, propylene, 1-butene, 1,3-butadiene, allene, 1-pentene, phenylethylene, p-chlorophenylethylene, cyclohexene, and cyclopentene.

Free radical initiators suitable for the process of the invention are as follows:

a. Azonitriles having the formula

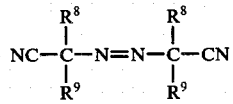

in which $R^8$ and $R^9$ are independently selected from the group consisting of $C_1$-$C_6$ alkyl, phenyl, phenylalkyl containing a $C_1$-$C_3$ alkyl, and $C_3$-$C_6$ cycloalkyl, or $R^8$ and $R^9$ conjointly form $C_3$-$C_9$ alkylene. Preferred among the azonitriles are those in which $R^8$ is $C_1$-$C_6$ alkyl or $C_3$-$C_6$ cycloalkyl, and $R^9$ is methyl, and those in which $R^8$ and $R^9$ conjointly form $C_6$-$C_9$ alkylene. Examples of suitable azonitriles are azobisisobutyronitrile, azobismethyl-n-amylacetonitrile, azobismethylisobutylacetonitrile, azobismethyl-t-butylacetonitrile, azobisdiisobutylacetonitrile, azobismethylcyclopropylacetonitrile, azobismethylcyclohexylacetonitrile, and those in which $R^8$ and $R^9$ conjointly form hexylene, heptylene, and nonylene groups.

b. Phosphites having the formula $(R^{10})_2POH$ or $(R^{10})_3P$ in which $R^{10}$ is selected from the group consisting of $C_1$-$C_6$ alkyl, $C_1$-$C_6$ alkoxy, phenoxy, and phenylthio. Preferred among the phosphites are those in which $R^{10}$ is selected from the group consisting of $C_1$-$C_3$ alkyl, $C_1$-$C_3$ alkoxy, phenoxy, and phenylthio. Examples of suitable phosphites are dimethylphosphite, diethylphosphite, trimethylphosphite, triethylphosphite, triphenylphosphite, and triphenylthiophosphite.

c. Ketones having the formula

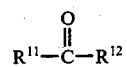

in which $R^{11}$ and $R^{12}$ are independently selected from the group consisting of $C_1$-$C_6$ alkyl, phenyl, and phenylalkyl containing a $C_1$-$C_3$ alkyl. Preferred among this group are those ketones in which $R^{11}$ and $R^{12}$ are independently $C_1$-$C_4$ alkyl, benzyl or phenyl. Examples of suitable ketones are benzophenone, acetophenone, 2-pentanone, 3-pentanone, 1-phenyl-1-propanone, isobutyrophenone, and 1,3-diphenyl-2-propanone.

d. Diones having the formula

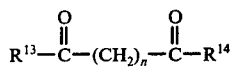

in which $R^{13}$ and $R^{14}$ are independently selected from the group consisting of $C_1$-$C_6$ alkyl and phenyl, and $n$ is an integer from 0 to 6, inclusive. Preferred among this group are the diones in which $n$ is 0. Examples are 2,3-butanedione, 2,3-pentanedione, and 3,4-hexanedione.

3. Substituted or unsubstituted aromatic compounds selected from the group consisting of phenanthrene, naphthalene, and quinoline; wherein the substituents are halo or methyl. Examples of substituted members of this group are 1-methylnaphthalene, 1-chloronaphthalene, and 2-chloroquinoline.

As used in this specification:

the term "alkyl" represents a monovalent saturated aliphatic hydrocarbon group formed from a straight- or branched-chain alkane having the specified number of carbon atoms with one hydrogen removed at the point of bonding to the remainder of the molecule; for example, methyl, ethyl, n-propyl, or isopropyl;

the term "alkenyl" represents a monovalent aliphatic hydrocarbon group containing at least one double bond, formed from a straight- or branched-chain alkene having the specified number of carbon atoms with one hydrogen removed at the point of bonding; for example, vinyl, allyl, butenyl, or butadienyl;

the term "alkynyl" represents a monovalent aliphatic hydrocarbon group containing at least one triple bond, formed from a straight- or branched-chain alkyne having the specified number of carbon atoms with one hydrogen removed at the point of bonding; for example, ethynyl, propynyl, or 3-butynyl;

the term "aryl" represents a monovalent monocyclic or bicyclic aromatic hydrocarbon group, formed from benzene, or naphthalene with one hydrogen removed at the point of bonding;

the term "aralkyl" represents an alkyl group as defined above, in which a second hydrogen is substituted by an aryl group as defined above, for example, benzyl, phenethyl, or naphthylmethyl;

the term "cycloalkyl" represents a monovalent cyclical saturated hydrocarbon group, formed from a cycloalkane having the specified number of carbon atoms with one hydrogen removed at the point of bonding; for example, cyclopropyl, cyclobutyl, cyclopentyl, or cyclohexyl;

the term "cycloalkenyl" represents a monovalent cyclical hydrocarbon group containing at least one double bond, formed from a cycloalkene having the specified number of carbon atoms with one hydrogen removed at the point of bonding; for example, cyclohexenyl or cycloheptenyl;

the term "alkoxy" represents an alkyl group as defined above with an oxygen atom separating the group from the remainder of the molecule at the point of bonding; for example, methoxy, ethoxy, or isopropoxy;

the term "alkenoxy" represents an alkenyl group as defined above with an oxygen atom separating the group from the remainder of the molecule at the point of bonding; for example, butenoxy;

the term "alkoxyalkyl" represents an alkyl group as defined above, in which a second hydrogen is substituted by an alkoxy group as defined above; for example, methoxymethyl, or ethoxymethyl;

the term "alkylthioalkyl" represents an alkyl group as defined above, in which a second hydrogen is substituted by a sulfur atom bonded to a second alkyl group as defined above; for example, ethylthiomethyl;

the term "alkoxyalkenyl" represents an alkenyl group as defined above, in which a second hydrogen is substituted by an alkoxy group as defined above; for example, methoxyvinyl or ethoxyvinyl;

the term "alkylthioalkenyl" represents an alkenyl group as defined above, in which a second hydrogen is substituted by a sulfur atom bonded to an alkyl group as defined above; for example, methylthiovinyl;

the terms "halogen" and "halo" represent fluorine, chlorine, bromine, or iodine;

the term "alkylene" represents a bivalent saturated aliphatic hydrocarbon group formed from a straight-chain alkane having the specified number of carbon atoms with a hydrogen removed at each end; for example, methylene, ethylene, or propylene;

the term "alkenylene" represents a bivalent aliphatic hydrocarbon group containing at least one double bond, formed from a straight-chain alkene having the specified number of carbon atoms with a hydrogen removed at each end; for example butenylene;

the term "heterocyclic ring group" refers to a monovalent group containing both carbon atoms and non-carbon atoms joined together to form a monocyclic, bicyclic, or tricyclic ring of 3 to 8 atoms per cycle, saturated or containing one or more double bonds, in which the term "non-carbon atoms" refers to nitrogen, phosphorus, or sulfur atoms, or any combination thereof; for example, pyrryl, pyrrolydyl, pyrazolyl, aziridinyl, oxazolydyl, and thiazolydyl.

All carbon atom ranges stated herein are intended to be inclusive of both upper and lower limits.

DETAILED DESCRIPTION OF THE INVENTION

The process of the present invention entails a series of reactions occuring simultaneously in the same reaction vessel. The first is the reaction between the amine shown above and carbonyl sulfide to produce a thiolcarbamic acid. A free radical initiator acts on the thiolcarbamic acid to produce a radical of the formula

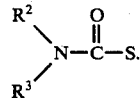

The following description shows the use of a terminal alkene, $CH_2=CH-R^6$, unsaturated compound. Analogous mechanisms result when any of the other unsaturated compounds described above are used.

The radical shown above reacts with the alkene to produce a second radical of the formula

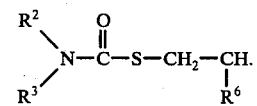

The latter subsequently reacts with an additional molecule of thiolcarbamic acid to produce the desired thiolcarbamate and simultaneously regenerate the thiolcarbamic acid radical shown above.

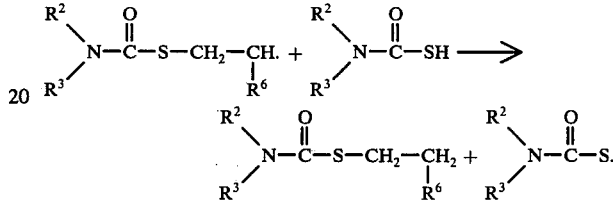

The amount of carbonyl sulfide used relative to the amine is not a critical feature of the invention. The COS/amine ratio can vary over a wide range. However, the amine salt of the thiolcarbamic acid is formed by reaction of the acid with an additional molecule of the amine. This is an undesirable side reaction of the process since it disrupts the free radical chain reaction. Since the amine salt exists in equilibrium with the thiolcarbamic acid, the equilibrium can be shifted in favor of the thiolcarbamic acid by the presence of an excess of carbonyl sulfide. The quantity of salt present is thereby reduced, and the quantity of thiolcarbamic acid increased, thus increasing the number of free radical generation cycles as indicated above. Thus, the efficiency of the process will increase as the COS/amine ratio is increased. Preferably, the COS/amine mole ratio is greater than 1.0.

The carbonyl sulfide can be used as such or it can be generated in situ by reaction of sulfur and carbon monoxide.

The free radical reaction itself proceeds independently of both temperature and pressure, hence no critical ranges exist for either of these two variables. The reaction rate may be benefited, however, by increasing the system temperature or COS pressure, or both. The temperature is limited at the lower extreme only by the freezing point of the system and at the upper extreme only by the spontaneous generation of free radicals leading to increased impurities, and the disproporationation of carbonyl sulfide into $CO_2$ and $CS_2$. The pressure is limited only by considerations of economy and the limitations of materials of construction used. Other than these considerations, it will be most convenient to run the reaction at a temperature between about 0° C and about 100° C, and a pressure between about atmospheric and 150 pounds per square inch gauge.

Although frequently unnecessary, a solvent may be used when convenience is enhanced thereby, for example to dissolve a gaseous alkene. Any non-reactive solvent can be used. Preferred solvents are those characterized by low volatility and high solubility of the amine and alkene. Suitable solvents include alkanes of six carbon atoms or higher, aromatic compounds such as benzene and toluene, and alcohols such as ethyl alcohol, propyl alcohol, and butyl alcohol.

The product yield bears no relation to the relative quantities of alkene and amine. The yield can be impaired, however, by the presence of impurities in the system which will react with the free radicals generated, preventing them from proceeding along the desired course as indicated above.

The amount of free radical initiator which will be used is not critical. However, it will be obvious to one skilled in the art that the formation of the desired thiolcarbamate will be enhanced as the amount of free radical initiator is increased. For some systems, a combination of free radical initiators will perform better than any one used alone, for example: a ketone/phosphite combination, or an azonitrile/phosphite combination. In addition, the activity of some free radical initiators can be enhanced by the use of ultraviolet light. In a preferred embodiment, one or more free radical initiators are used in conjunction with ultraviolet light. Typical wave lengths of ultraviolet light are found in the range of about 2,500 to about 3,300 angstroms.

At the termination of the reaction, unreacted amine can be removed from the system by a dilute acid wash, solvents and other volatiles can be removed by evaporation, and remaining liquid impurities can be removed by conventional liquid separation techniques such as distillation, etc.

The following examples are offered to further illustrate the process of the invention.

EXAMPLES

The following general procedure was used:

In Examples 1 through 10, cyclohexene was used as the unsaturated compound, and was placed in a 500 ml glass pressure vessel together with di-n-propylamine and the free radical initiator. The vessel was then sealed, chilled to about 0° C, and saturated with COS. The relative amounts of COS, amine and cyclohexene are shown in the following table. The cooling bath was then removed and the system was illuminated overnight by seven F15T8 B1 15-watt fluorescent ultraviolet lights, with emissions peaking at approximately 3000 A. The pressure was then released. The resulting mixture was washed with dilute aqueous HCl to remove unreacted amine. Residual acid was then removed with a water wash. Unreacted cyclohexene was removed under reduced pressure. The resulting product was analyzed by gas chromatography.

In Examples 11 through 16, ethylene was used as the unsaturated compound. The reaction vessel was charged with di-n-propylamine, a solvent, and the free radical initiator. The vessel was then sealed and chilled to about 0° C. The vessel was then saturated with COS and subsequently pressurized with ethylene up to about 30-40 pounds per square inch gauge (equivalent to about 30,000 to about 40,000 Pascals). The cold bath was then removed and the vessel was illuminated overnight as described above. The pressure was then released and the product recovered as described above, with reduced pressure used to remove the solvent.

The results are shown in the following table.

| | RESULTS | | | | | |
|---|---|---|---|---|---|---|
| | Reactant Mole Ratios | | | | Yield | Purity |
| Experiment | Alkene/Amine | COS/Amine | Free Radical Initiator | Solvent | (%) | (%) |
| Using di-n-propylamine and cyclohexene: | | | | | | |
| 1 | 4.0 | | $(C_2H_5O)_2POH$, Vazo®[a], UV[b] | none | 2.0[c] | 18 |
| 2 | 4.0 | 1.7 | $(CH_3O)_3P$, $(CH_3)_2CO$, UV | none | 1.6 | 67 |
| 3 | 4.0 | | 2,3-butanedione, UV | none | 3.6 | 12 |
| 4 | 4.0 | 1.2 | $(C_2H_5O)_3P$, 3-pentanone, UV | none | 7.9 | 1 |
| 5 | 15.8 | 8.3 | $(C_6H_5S)_3P$, benzophenone, UV | none | 13.5[d] | 20 |
| 6 | 4.0 | 4.0 | $(C_2H_5O)_3P$, benzophenone, UV | none | 22.1[d] | 58 |
| 7 | 2.4 | 8.0 | $(C_2H_5O)_3P$, benzophenone, UV | none | 8.5[d] | 62 |
| 8 | 4.0 | 8.0 | $(C_2H_5O)_3P$, benzophenone, UV | none | 22.0[d] | 32 |
| 9 | 4.0 | 8.0 | $(C_2H_5O)_3P$, naphthalene, UV | none | 4.3 | 3 |
| 10 | 4.0 | 2.1 | $(C_2H_5O)_3P$, acetophenone, UV | none | 3.3 | 11 |
| Using di-n-propylamine and ethylene: | | | | | | |
| 11 | 0.30 | 1.0 | $(C_2H_5O)_3P$, 3-pentanone, UV | toluene | 8.3[e] | 49 |
| 12 | 0.46 | 1.0 | $(C_2H_5O)_3P$, 3-pentanone, UV | ethanol | 2.3 | 56 |
| 13 | 0.40 | 1.0 | $(C_2H_5O)_3P$, 3-pentanone, UV | ethanol | 6.9 | 27 |
| 14 | 0.46 | 1.1 | 3-pentanone, UV | toluene | 2.8 | 3 |
| 15 | 0.62 | 1.1 | $(C_2H_5O)_3P$, 3-pentanone, UV | hexane | 0.7 | 44 |
| 16 | 0.69 | 1.3 | $(C_2H_5O)_3P$, 3-pentanone, UV | benzene | 2.6 | 38 |

[a]2,2'-azobis(isobutyronitrile) (E.I. Dupont de Nemours & Co.)
[b]Ultraviolet light
[c]In Examples 1-10, the yield is based on the amine.
[d]Figure includes benzophenone
[e]In Examples 11-16, the yield is based on ethylene.

What is claimed is:

1. A process for the manufacture of a thiolcarbamate having the formula

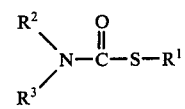

in which

R[1] is selected from the group consisting of —CH$_2$—CH=CR[4]R[5], —CH$_2$—CH$_2$—R[6], and

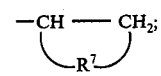

R[2] and R[3] are independently selected from the group consisting of the following substituted or unsubstituted groups: $C_1$-$C_{10}$ alkyl, $C_2$-$C_6$ alkenyl, $C_2$-$C_4$ alkynyl, aralkyl containing a $C_1$-$C_6$ alkyl, and $C_3$-$C_7$ cycloalkyl; wherein the substituents are independently selected from the group consisting of halo, cyano, nitro, trifluoromethyl, $C_1$-$C_4$ alkoxy, and $C_1$-$C_4$ alkyl; or R² and R³ are joined to each other to form, together with the nitrogen atom, a nitrogen-containing heterocyclic ring;

R⁴, R⁵, and R⁶ are independently selected from the group consisting of hydrogen and the following substituted or unsubstituted groups: $C_1$-$C_{10}$ alkyl, $C_2$-$C_6$ alkenyl, $C_2$-$C_4$ alkynyl, aryl, aralkyl containing a $C_1$-$C_6$ alkyl, $C_3$-$C_7$ cycloalkyl, $C_5$-$C_7$ cycloalkenyl, $C_1$-$C_{10}$ alkoxy, $C_2$-$C_6$ alkenoxy, $C_2$-$C_{10}$ alkoxyalkyl, $C_2$-$C_{10}$ alkylthioalkyl, $C_3$-$C_{10}$ alkoxyalkenyl, $C_3$-$C_{10}$ alkylthioalkenyl, and heterocyclic ring groups; wherein the substituents are independently selected from the group consisting of halo, cyano, nitro, trifluoromethyl, $C_1$-$C_4$ alkoxy, and $C_1$-$C_4$ alkyl; and R⁷ is selected from the group consisting of $C_1$-$C_5$ alkylene and $C_3$-$C_5$ alkenylene;

which comprises reacting a secondary amine having the formula

in which R² and R³ are as defined above, with carbonyl sulfide and an unsaturated compound selected from the group consisting of

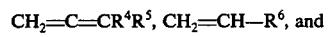

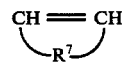

in which R⁴, R⁵, R⁶, and R⁷ are as defined above, in the presence of at least one free radical initiator selected from the group consisting of a. an azonitrile having the formula

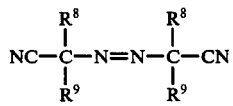

in which R⁸ and R⁹ are independently selected from the group consisting of $C_1$-$C_6$ alkyl, phenyl, phenylalkyl containing a $C_1$-$C_3$ alkyl, and $C_3$-$C_6$ cycloalkyl; or R⁸ and R⁹ conjointly form $C_3$-$C_9$ alkylene;

b. a phosphite having the formula $(R^{10})_2POH$ or $(R^{10})_3P$ in which $R^{10}$ is selected from the group consisting of $C_1$-$C_6$ alkyl, $C_1$-$C_6$ alkoxy, phenoxy, and phenylthio;

c. a ketone in the presence of ultraviolet light, said ketone having the formula

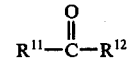

in which $R^{11}$ and $R^{12}$ are independently selected from the group consisting of $C_1$-$C_6$ alkyl, phenyl, and phenylalkyl containing a $C_1$-$C_3$ alkyl;

d. a dione having the formula

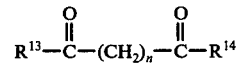

in which $R^{13}$ and $R^{14}$ are independently selected from the group consisting of $C_1$-$C_6$ alkyl and phenyl, and $n$ is an integer ranging from 0 to 6;

e. a substituted or unsubstituted aromatic compound selected from the group consisting of phenanthrene, naphthalene, and quinoline; wherein the substituents are halo or methyl.

2. A process according to claim 1 in which R¹ is selected from the group consisting of

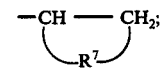

R² and R³ are independently selected from the group consisting of $C_1$-$C_5$ alkyl, $C_2$-$C_4$ alkenyl, and $C_4$-$C_6$ cycloalkyl, or R² and R³ joined together form with the nitrogen atom the group

in which R° is $C_4$-$C_6$ alkylene;

R⁶ is selected from the group consisting of hydrogen and $C_1$-$C_3$ alkyl; and

R⁷ is $C_3$-$C_5$ alkylene.

3. A process according to claim 1 in which the mole ratio of carbonyl sulfide to amine is greater than 1.0.

4. A process according to claim 1 in which the reaction occurs at a temperature between about 0° C and about 100° C.

5. A process according to claim 1 in which the reaction is conducted in the presence of ultraviolet light.

6. A process according to claim 1 in which R¹ is ethyl, R² is n-propyl, and R³ is n-propyl.

7. A process according to claim 1 in which R¹ is cyclohexyl, R² is n-propyl, and R³ is n-propyl.

8. A process according to claim 1 in which R¹ is ethyl, and R² and R³ conjointly form hexylene.

9. A process according to claim 1 in which R¹ is ethyl, R² is isobutyl, and R³ is isobutyl.

10. A process according to claim 1 in which R¹ is n-propyl, R² is n-propyl, and R³ is n-propyl.

11. A process according to claim 1 in which R¹ is ethyl, R² is ethyl, and R³ is cyclohexyl.

12. A process according to claim 1 in which R¹ is n-propyl, R² is n-butyl, and R³ is ethyl.

* * * * *

UNITED STATES PATENT AND TRADEMARK OFFICE
CERTIFICATE OF CORRECTION

PATENT NO. : 4,071,423
DATED : January 31, 1978
INVENTOR(S) : Harold M. Pitt

It is certified that error appears in the above-identified patent and that said Letters Patent are hereby corrected as shown below:

In Column 3, at line 4, after the words "consisting of" please insert the words "$-CH_2-CH_2-R^6$ and"

Signed and Sealed this

Thirtieth Day of May 1978

[SEAL]

Attest:

RUTH C. MASON
Attesting Officer

LUTRELLE F. PARKER
Acting Commissioner of Patents and Trademarks